United States Patent [19]

Daum et al.

[11] Patent Number: 4,912,985
[45] Date of Patent: Apr. 3, 1990

[54] GAS SAMPLING SYSTEM FOR REACTIVE GAS-SOLID MIXTURES

[75] Inventors: Edward D. Daum; William Downs, both of Alliance; Bryan J. Jankura, Mogadore; John M. McCoury, Jr., Mineral City, all of Ohio

[73] Assignee: The Babcock & Wilcox Company, New Orleans, La.

[21] Appl. No.: 348,227

[22] Filed: May 5, 1989

Related U.S. Application Data

[62] Division of Ser. No. 235,358, Aug. 23, 1988, Pat. No. 4,856,352.

[51] Int. Cl.⁴ .............................................. G01N 1/22
[52] U.S. Cl. ......................... 73/863.25; 73/863.33
[58] Field of Search .................. 73/1 G, 23, 863.12, 73/863.21, 863.23, 863.24, 863.25, 863.31, 863.33, 863.81, 863.85, 863.43, 864.73

[56] References Cited

U.S. PATENT DOCUMENTS

| | | | |
|---|---|---|---|
| 3,106,843 | 10/1963 | Luxl | 73/863.12 |
| 4,094,187 | 6/1978 | Navarre, Jr. | 73/1 G |
| 4,154,088 | 5/1979 | Werner | 73/863.12 X |
| 4,279,142 | 7/1981 | McIntyre | 73/1 G |
| 4,342,234 | 8/1982 | Bernath | 73/863.12 |
| 4,485,684 | 12/1984 | Weber et al. | 73/863.12 |
| 4,578,986 | 4/1986 | Navarre | 73/1 G |
| 4,586,390 | 5/1986 | Helke | 73/864.73 |
| 4,756,200 | 7/1988 | Ramsner et al. | 73/864.73 X |

*Primary Examiner*—Tom Noland
*Attorney, Agent, or Firm*—Vytas R. Matas; Robert J. Edwards; Daniel S. Kalka

[57] ABSTRACT

An apparatus and method for sampling gas containing a reactive particulate solid phase flowing through a duct and for communicating a representative sample to a gas analyzer. A sample probe sheath 32 with an angular opening 34 extends vertically into a sample gas duct 30. The angular opening 34 is opposite the gas flow. A gas sampling probe 36 concentrically located within sheath 32 along with calibration probe 40 partly extends in the sheath 32. Calibration probe 40 extends further in the sheath 32 than gas sampling probe 36 for purging the probe sheath area with a calibration gas during calibration.

3 Claims, 2 Drawing Sheets

GAS SAMPLING SYSTEM FOR REACTIVE GAS-SOLID MIXTURES

This is a division of application Ser. No. 07/235,358 filed 8/23/88, now Pat. No. 4,856,35,2.

BACKGROUND OF THE INVENTION

FIELD OF THE INVENTION

The present invention relates in general to a system for sampling gas and, in particular, is directed to a system for sampling a gas containing a reactive particulate solid phase such that essentially all of the solids are removed in such a manner that the gas phase composition is essentially unchanged. Thus, a representative gas sample is obtained for determining its composition by a gas analyzer.

DESCRIPTION OF THE RELATED ART

Gas sampling systems are available from several vendors such as E. I. DuPont, etc., for use with gas analyzers. These systems, when designed for dust-laden gases, clean the gas by filtration through a mesh screen or porous media. Where chemical reactions between the gas and particulate matter potentially exist, these systems inadvertently allow these chemical reactions to alter the chemical composition of the gas sample by providing an intimate contact zone. Thus, the gas analysis equipment measures gas concentrations unrepresentative of the bulk gas stream.

Flue gas from fossil fuel fired boilers is one example of this kind of gas-solid mixture. Recent concerns and awareness in our environment have led to new efforts to refine our boiler technology with the removal and/or reduction of air pollutants such as particulates, sulfur oxides ($SO_x$), and oxides of nitrogen ($NO_x$).

During the combustion of fossil fuel, various combustion off-gases are produced which contain a variety of contaminants such as sulfur dioxide, sulfur trioxide, and fly ash. U.S. Pat. No. 4,452,765, which is assigned to the assignee of the present invention, discloses a method for removing sulfur oxides from a hot flue gas by introducing an alkali slurry. This patent is hereby incorporated by reference. The present invention finds particular utility in sampling the gas stream at various points in that system to maintain air pollution emission control standards.

Accurate monitoring of the flue gas is required to be sure that methods like this or newly developed ones are effective so that as a minimum they improve the quality of the emission. A representative sample of the gas is necessary for an accurate analysis.

The prior art has recognized some of the problems of analyzing dust-laden gas samples. U.S. Pat. No. 4,485,684 issued to Weber, et al discloses an apparatus for extracting and analyzing dust-laden gas samples. The device employs a stilling chamber tapered downwards in the shape of a horizontal half-funnel in the direction of the flow of the gas. Flanges connect the stilling chamber to a gas sample extraction pipe or sample probe from an exhaust gas line. The gas sample extraction probe of conventional construction extends coaxially in the connecting pipe. A conveying pipe which is connected to a three-way valve acts as a switching valve and connects the gas probe to a conventional filter. From the filter the gas sample goes through a gas feed pump to a gas analyzer. A time control device connected to the three-way valve permits cleaning with compressed air at specific intervals.

A different approach to this problem was used in U.S. Pat. No. 3,106,843, issued to Luxl. This reference discloses an atmosphere sampling probe for gas analyzers to obtain continuous flow of the sample stream. The clogging of the probe during extended periods of operation is prevented by utilizing steam which condenses about the solid particles in the sample stream. Water is supplied to separate the steam by condensing it as well as washing the gas sample of corrosive materials.

Both of these references only address the problem of the filters clogging or plugging with dust. None of these prior art systems recognize the problem that chemical reactions occur between the gas and the particulate material. Nor is the prior art directed to a gas sampling system for sampling a gas containing a reactive solid phase such that the majority of the solids are removed in such a fashion that the gas phase composition is essentially unchanged and is thereby representative of the gas sampled at the initial sampling point.

SUMMARY OF THE INVENTION

The present invention provides an apparatus and method for sampling a gas containing a reactive solid phase flowing through a duct and for communicating a representative sample to a gas analyzer. The apparatus comprises a sample probe sheath extending vertically into the top of a gas duct. The sample probe sheath has an angular opening at one end with the opening extending in the opposite direction of the gas flow. A gas sampling probe partially extends into the sample probe sheath. A calibration probe connected to a calibration gas line extends into the sample probe sheath with the calibration probe extending further in the sample probe sheath than the gas sampling probe. At least one filter is connected between the gas sampling probe and a gas analyzer.

The calibration probe extends further in the sample probe sheath than the gas sampling probe for purging the sample probe sheath with the calibration gas during calibration. Both the calibration and gas sampling probes are sealed at the closed end of the sample probe sheath. The apparatus includes a means for maintaining the temperature range which surrounds the apparatus to minimize gas-solids reactions.

Another aspect of the present invention is directed to a method for sampling a gas containing a reactive solid phase and flowing through a duct to communicate a representative sample to a gas analyzer. The method includes the steps of aspirating a gas containing a reactive particulate solid phase into a primary separation zone in a sample probe sheath, and drawing a sample into a sample probe located within the sample probe sheath. Maintaining the temperature within a range which minimizes gas-solids reactions provides for the continuous representative monitoring of the gas concentration. Periodic calibration of the gas analyzer is provided by the calibration probe which discharges a predetermined concentration of gas constituents into the sample probe sheath at a flow rate in excess of the gas sampling rate.

Advantageously, the gas sampling configuration of the present invention allows continuous, representative monitoring of gas concentrations and eliminates damage or drift to instrumentation from solids. Easy access to the filter assembly minimizes downtime when filter changes are required.

The various features of novelty characterized in the invention are pointed out with particularity in the claims annexed to and forming a part of this disclosure. For a better understanding of the invention, and the operating advantages obtained by its use, reference is made to the accompanying drawings and descriptive matter in which the preferred embodiment of the invention is illustrated.

DESCRIPTION OF THE PREFERRED EMBODIMENT

Figure 1:
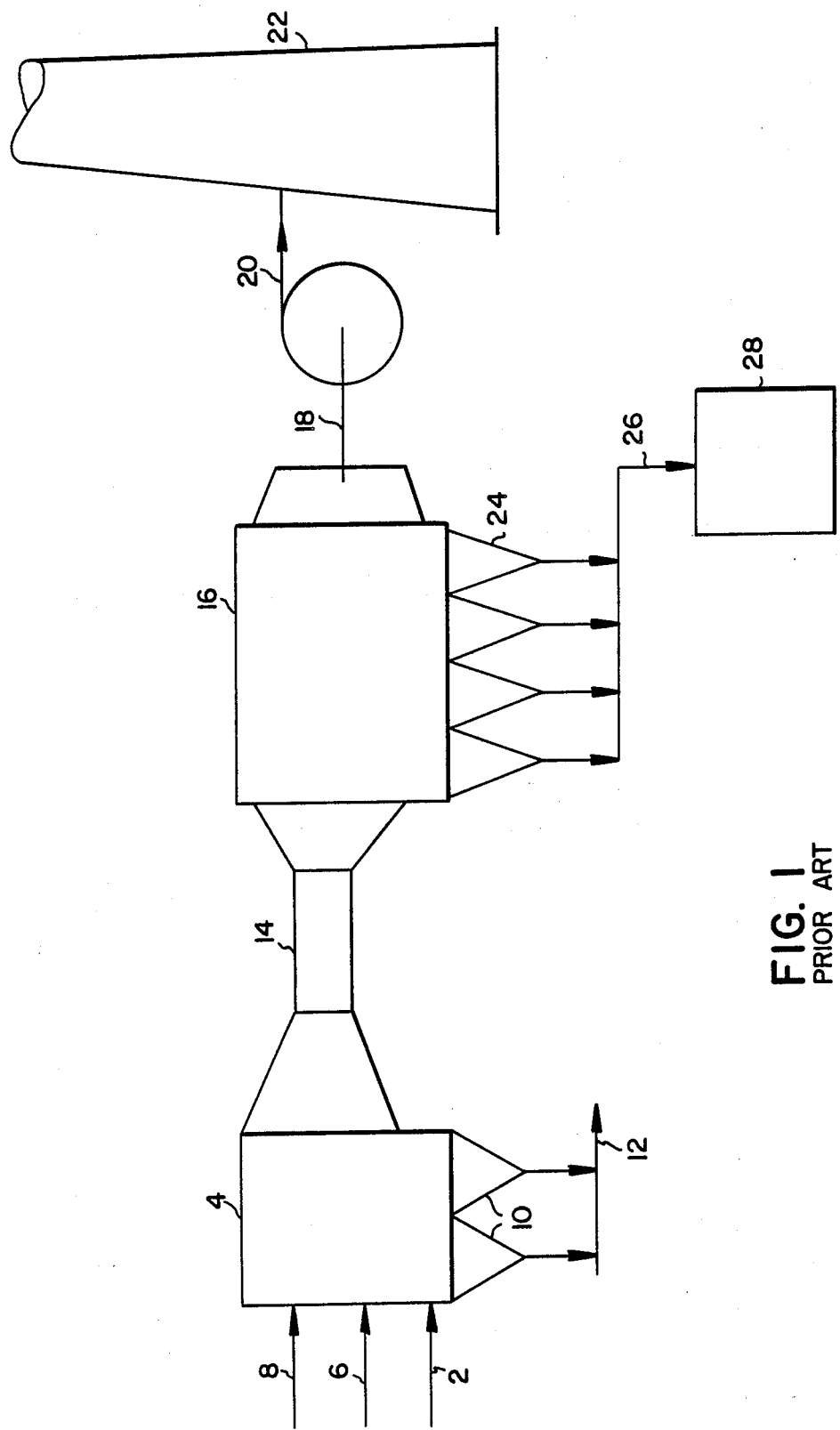
FIG. 1 is a schematic block diagram of a portion of a representative boiler system where the present invention is employed to monitor flue gas emission.

Referring to FIG. 1, there is illustrated a schematic representation of the air pollution control components in a conventional boiler system. Hot flue gas derived from the combustion of fossil fuel is conveyed from a combustion zone, not shown but well known in the art, through conduit 2 to spray drying reactor chamber 4. Steam or air supplied by a source not shown is conveyed by conduit 6 to spray drying reactor chamber 4. The alkali slurry supplied by a system disclosed in U.S. Pat. No. 4,452,765 is delivered to spray drying reactor chamber 4 by means of conduit 8.

The hot flue gas is treated in the fashion as described in U.S. Pat. No. 4,452,765. Settleable particulate matter is removed by gravity for collection in ash hopper 10 where it is conveyed by conduit 12 for ultimate disposal.

The flue gas exits the spray drying reactor chamber 4 passing through a gas reheat zone 14 for gas reheat when required for corrosion control in dry particle collection zone 16. The dry particle collection is achieved with the use of an electrostatic precipitator, a fabric filter, or the like. The treated gas leaves the dry particle collection zone 16 through conduit 18 substantially free of particulate matter and sulfur oxides. The flue gas is then pumped through conduit 20 to an exhaust stack 22 for atmospheric discharge.

Reacted alkali particles and fly ash that are collected in ash hoppers 24 are conveyed by conduit 26 to reprocessing zone 28 for reprocessing and recycling.

Monitoring the flue gas such as in the gas reheat zone 14, and conduits 18, 20 at several points in the system reveals the effectiveness of the pollution control technique. For purpose of this invention, the term "duct or gas duct" is meant to include the above-mentioned points in a boiler system.

Figure 2:
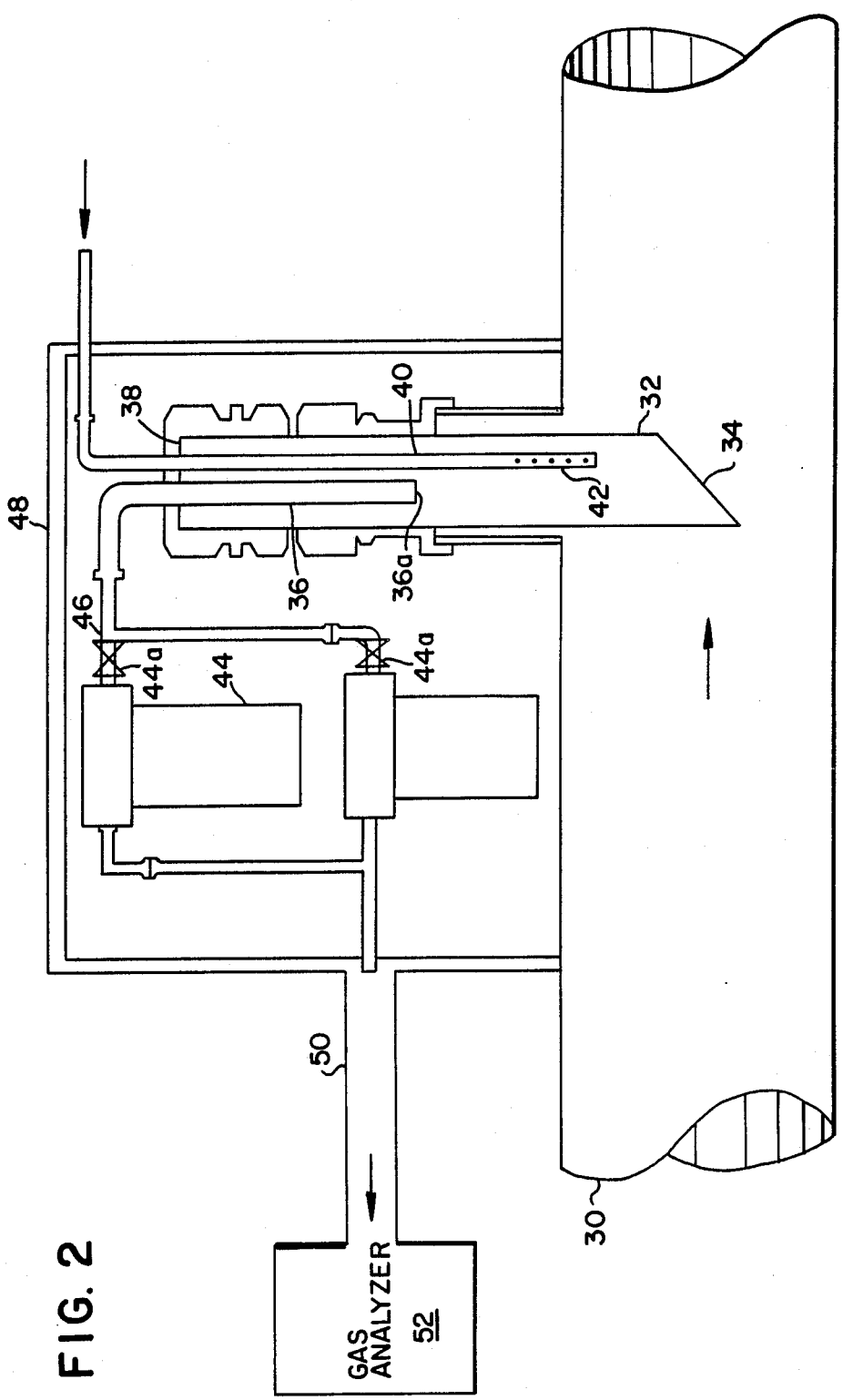
FIG. 2 is a cross-sectional illustration of the preferred embodiment of the present invention in place on a gas duct.

With reference to FIG. 2, a gas-solid mixture normally travels through a gas duct 30 with the arrow in duct 30 indicating the direction of flow of the gas-solid mixture. A sample probe sheath 32 extends into the sample gas duct 30. The sample probe sheath has an angular opening 34 at one end with the opening 34 being in the opposite direction of the gas flow as shown by the arrow in gas duct 30. An opening with a 45° angle is preferred. Other angles are usable with probably no significant consequence. A 45° angle is easy to cut, i.e., it is a mitered corner. Alternate geometries can be envisioned such as a closed pipe with a slot opening on the downstream side. However, the angled cut is preferred for cleaning purposes.

The vertically orientated sample probe sheath 32 has a sufficient inner diameter to allow for a primary separation of the particulate solids which accompany the gas sample. In a pilot test, a diameter of 2½ inches was suitable for a 12 inch gas duct. In the boiler industry, ducts of varying size are encountered and so the emphasis shifts to compliance with the Environmental Protection Agency continuous emission monitoring standards (CEMS). The sample probe sheath 32 extends into a gas duct 30 to a representative location of the gas stream. The sample probe sheath 32 is completely sealed from possible infiltration of ambient air at its opposite end 38.

A conventional gas sampling probe 36 passes through the sample probe sheath end connection 38. The gas sampling probe draws a partially clean, i.e., reduced particulate concentration of gas-solid mixture from the primary separation zone which is defined as, a point between the sample probe sheath inlet 34 and the end of the gas sampling probe 36a. The distance from the end of the gas sampling probe 36a to the sample probe sheath inlet 34 may range conveniently from three to eight sample probe sheath inner diameters, but can be a greater distance if sample response times are not critical to the application. A point midway in the sample probe sheath 32 is preferred.

The calibration probe 40 passes through the sample probe sheath end connection 38 for optional delivery of an appropriate calibration gas. One end of the calibration probe 40 is connected to a source for calibration gas (not shown). The calibration line outlet 42 which has a plurality of small apertures discharges into the primary separation zone. A calibration gas at a sufficient volumetric flow rate to purge this area of the sample probe sheath 32 is injected while a calibration gas is drawn into the gas sample probe 36. The calibration gas flow rate must be greater than the sample gas flow rate to insure that this probe sheath 32 is flooded with calibration gas.

The gas sample probe 36 delivers the gas-solid mixture from the primary separation zone to the filter elements 44 through gas line 46. These filters 44 contain media filters which remove a minimum of 99.99% of the entering solids having a diameter equal to or greater than 0.1 microns.

As shown in FIG. 2, two filters 44 are used in parallel to each other. Originally, this arrangement was intended to use one filter at a time with the other as a spare. When it became necessary to change that filter, the operator would switch flow over to the spare filter by a valving arrangement 44a and then replace the used filter when the spare filter became clogged. Due to the amount of time a filter lasts, it was later found merely convenient to simply operate with both filters in parallel. Any number of filters or filter sizes in a suitable arrangement can be used.

In the preferred embodiment, the filters 44 are Balston ® type BH filters Type 37/12. These filters have an inorganic binder and are recommended for sample filtrations above 300° F., to a maximum temperature of 900° F.

The filters 44 including line 46 along with the gas sampling probe 36 and calibration probe 38 and the upper portion of the sample probe sheath 32 are maintained within a temperature range to minimize gas-solids reactions (either above or below the gas flow temperature) by the oven 48. These types of ovens which can maintain a temperature range above or below the flow temperature are well known.

The common filter outlet of gas line 46 as it exits filters 44 is connected to a heated hose or other suitable tube 50 to deliver the filtered gas to a conventional gas analyzer 52.

For most applications, the material contacting the gas are made of some grade of stainless steel.

The gas sampling apparatus described allows continuous, representative monitoring of gas concentrations and eliminates damage or drift to the instrumentation from particulate solids. Easy access to the multiple filter assembly minimizes or eliminates downtime when filter changes or maintenance are required.

The following are some example applications of the gas sampling system of the present invention.

One application of this sampling system involves its use with dry scrubbers. In dry scrubbers an aqueous slurry of calcium hydroxide, $Ca(OH)_2$, is sprayed into a hot flue gas (typically, about 300° F.) containing traces of sulfur dioxide, $SO_2$. The following reaction ensues within the dry scrubber:

$$Ca(OH)_2 + SO_2 \rightarrow CaSO_3 \cdot \tfrac{1}{2}H_2O + \tfrac{1}{2}H_2O \tag{I}$$

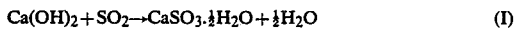

Typically, an excess of slurry is sprayed into the flue gas such that as the flue gas leaves the dry scrubber, moist particles of unreacted calcium hydroxide slurry flow coincident with the flue gas. At this point the flue gas is typically below about 200° F. and the relative humidity is above 10%. In a conventional sampling system, a small portion of the flue gas would be extracted from the flue or duct and would be directed to a filter where the calcium hydroxide solids would be separated from the gas sample. A cake of solids would rapidly accumulate on the filter. The reaction noted above, (I), would continue to occur. Thus, any gas sample passing through the filter would no longer contain a representative concentration of $SO_2$. The subject invention circumvents this problem in two ways. First, the method by which the flue gas is extracted, i.e., by requiring the flue gas to flow in reverse direction into the probe sheath causes an inertial separation of flue gas and slurry droplets. This serves to minimize (but not eliminate) the amount of solids which will reach and deposit on the filter. Secondly, experience has shown that the above reaction proceeds at a negligible rate when the relative humidity of the flue gas approaches zero. Therefore, by placing the external filter of this subject invention in a zone where the temperature is maintained between 250° F. and 350° F. this reaction can be minimized. As a result, the $SO_2$ concentration is not diminished as it passes across a filter cake of dry $Ca(OH)_2$.

Another benefit of the subject invention when compared to conventional filter based sampling systems is that frequent filter cleaning by various "blow back" procedures (as is usually used in commercial sampling systems) is not necessary. In-duct filters frequently require blow back every twenty minutes or so in order to prevent pluggage by the filter cake or to prevent significant sample degradation by accumulations of reactive solids. The subject invention minimizes the rate of accumulation of filter cake by the inertial separation step. That factor in combination with the temperature control which minimizes the reactivity of the filter cakes allows operation even in very dirty applications for up to several weeks before filter replacement becomes necessary. An added benefit of this fact is that media type filters can be used in place of sintered ceramic or metal filters which are used with blow back systems. Media filters (usually fiber glass) are much more effective filters and operate generally at much lower pressure drop than do the sintered type filters.

A second example of a system where the subject invention is applicable is in sampling flue gas in furnace sorbent injection applications. Typically, the reaction involved is represented by:

$$CaO + SO_2 + \tfrac{1}{2}O_2 \rightarrow CaSO_4 \tag{II}$$

This reaction is very rapid in the temperature range from about 1500° F. to about 2300° F. but diminishes to a negligible rate below about 700° F. Therefore, filtration at any temperature below about 700° F. should present no reaction problems via reaction (II). In principle, therefore, in-duct filters used in this temperature range should work adequately. However, because these in-duct filters must be cleaned by blow-back with compressed air, that filter is periodically cooled by the relatively cold compressed air to temperatures well below 700° F. When that happens, moisture can condense on the filter causing the deposits to become moist and therefore reactive via reaction (I). As in example one above, the subject invention avoids these problems by maintaining the filtration step at a temperature of about 300° F. and by avoiding the need for blow-back of the filter.

A third example of a system where this subject invention has been tested is on a wet scrubber utilizing a solution of sodium carbonate to react with $SO_2$ via:

$$Na_2CO_3 + SO_2 \rightarrow Na_2SO_3 + CO_2 \tag{III}$$

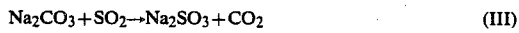

The sampling constraints here are similar to the first example. However, the reactivity of sodium carbonate is greater than $Ca(OH)_2$ and therefore, greater care must be taken in controlling the filtration temperature. By coincidence, 300° F. is the optimum temperature to filter sodium carbonate from the sampled flue gas.

The foregoing examples are intended for illustrative purposes and are not meant to limit the present invention only to these applications. The gas sampling system of the present invention has utility in any system where there exists a gas-solid mixture with the possible occurrence of gas-solid reactions.

While a specific embodiment of the invention has been shown and described in detail to illustrate the application of principles of the invention, certain modifications and improvements will occur to those skilled in the art upon reading the foregoing description. It is thus understood that all such modifications and improvements has been deleted herein for the sake of conciseness and readability but are properly in the scope of the following claims.

One example of such a modification would be to include a plurality of filters in parallel with valves directing the sampled gas to a predetermined filter or set of filters.

What is claimed is:

1. A method for sampling a gas containing a reactive particulate solid phase flowing through a duct and for communicating a representative sample to a gas analyzer, comprising the steps of:

situating a vertically orientated sample probe sheath so that it extends into the sample gas duct, the sample probe sheath having an angular opening at one end with the opening in the opposite direction of the gas flow;

establishing a primary separation zone by providing a gas sampling probe partially extending into the sample probe sheath;

situating a calibration probe which is connected to a calibration gas line to extend into the sample probe sheath substantially parallel to the gas sampling probe, the calibration probe extending further in the sample probe sheath than the gas sampling probe to allow for purging the sample probe sheath with a calibration gas;

aspirating the sample gas containing a reactive particulate solid phase into the primary separation zone;

drawing the sample into the sample probe;

delivering a representative sample through at least two filters to the gas analyzer, each of the filters being outside of the gas sample duct connected in parallel with respect to each other between the gas sampling probe and the gas analyzer with each of the filters further having a valve to allow for diverting sample gas flow for replacement of the filter; and maintaining a temperature range around a part of the gas sampling apparatus for minimizing reactions between the gas and solids, the maintained part being the sample probe sheath, the calibration probe, and the gas sampling probe outside of the gas duct, and the filters.

2. A method according to claim 1, further comprising the step of calibrating the primary separation zone with a calibration gas prior to the aspirating step.

3. A method as recited in claim 1, wherein the situating step includes a sample probe sheath with an angular opening of about 45°.

* * * * *